United States Patent [19]

Boomus et al.

[11] 4,111,807

[45] Sep. 5, 1978

[54] MOUTH FILTER FOR USE WITH PIPETTES

[75] Inventors: Mary Boomus, Chelsea; Bernard Sobin; Monty E. Vincent, both of Ann Arbor, all of Mich.

[73] Assignee: Gelman Instrument Company, Ann Arbor, Mich.

[21] Appl. No.: 840,685

[22] Filed: Oct. 11, 1977

Related U.S. Application Data

[63] Continuation-in-part of Ser. No. 768,450, Feb. 14, 1977, abandoned.

[51] Int. Cl.² ............... B01D 25/16; B01D 29/04; B01D 31/00
[52] U.S. Cl. ............... 210/152; 73/425.4 P; 210/251; 210/416 M; 210/446; 210/450; 210/451; 210/453; 210/462; 210/500 M; 422/100; 422/101
[58] Field of Search .... 210/416 R, 416 AS, 416 DW, 210/416 F, 416 L, 416 M, 418, 419, 420, 435, 445, 446, 450, 451, 453, 462, 463, 500 M, 251, 152; 23/259, 292; 128/233; 141/22–25, 27; 73/425.4 R, 425.4 P, 425.6

[56] References Cited

U.S. PATENT DOCUMENTS

| 2,376,231 | 5/1945 | Cohn | 73/425.4 P |
| 2,692,503 | 10/1954 | Crecelius | 73/425.4 P |
| 2,879,207 | 3/1959 | Poitras | 210/446 |

Primary Examiner—Frank Sever
Attorney, Agent, or Firm—Reising, Ethington, Barnard, Perry & Brooks

[57] ABSTRACT

In accordance with the invention there is provided a mouth filter for use with pipettes to insure that none of the liquid or any of the bacteria in the liquid being drawn into the pipette reach the mouth of the technician applying the suction. The filter comprises an organic resin housing having a filter membrane therein which divides the housing into an inlet chamber and an exit chamber, the filter membrane being hydrophobic and constituting a bacteria barrier. The housing has tubular extensions extending from the oppositely disposed axial end walls thereof. A tube is secured to one extension of the housing and is adapted to be secured in communicating relationship with a pipette into which the liquid is to be drawn. Connected to the other housing extension is a mouthpiece for mouth-applied suction by the technician, which suction is communicated through the filter membrane and tube to the pipette.

3 Claims, 3 Drawing Figures

U.S. Patent  Sept. 5, 1978  4,111,807
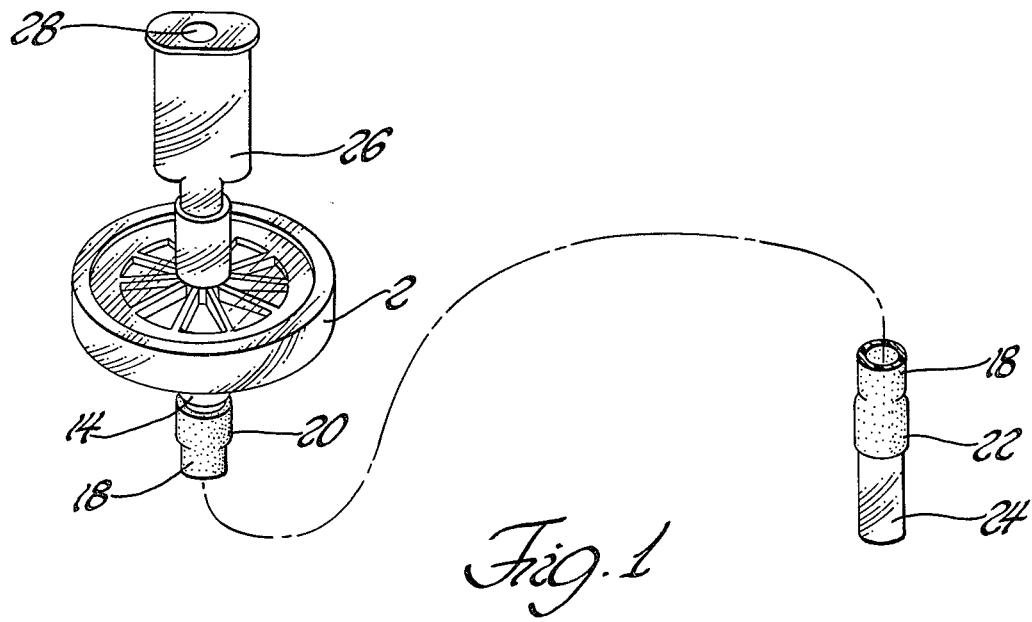
Fig. 1
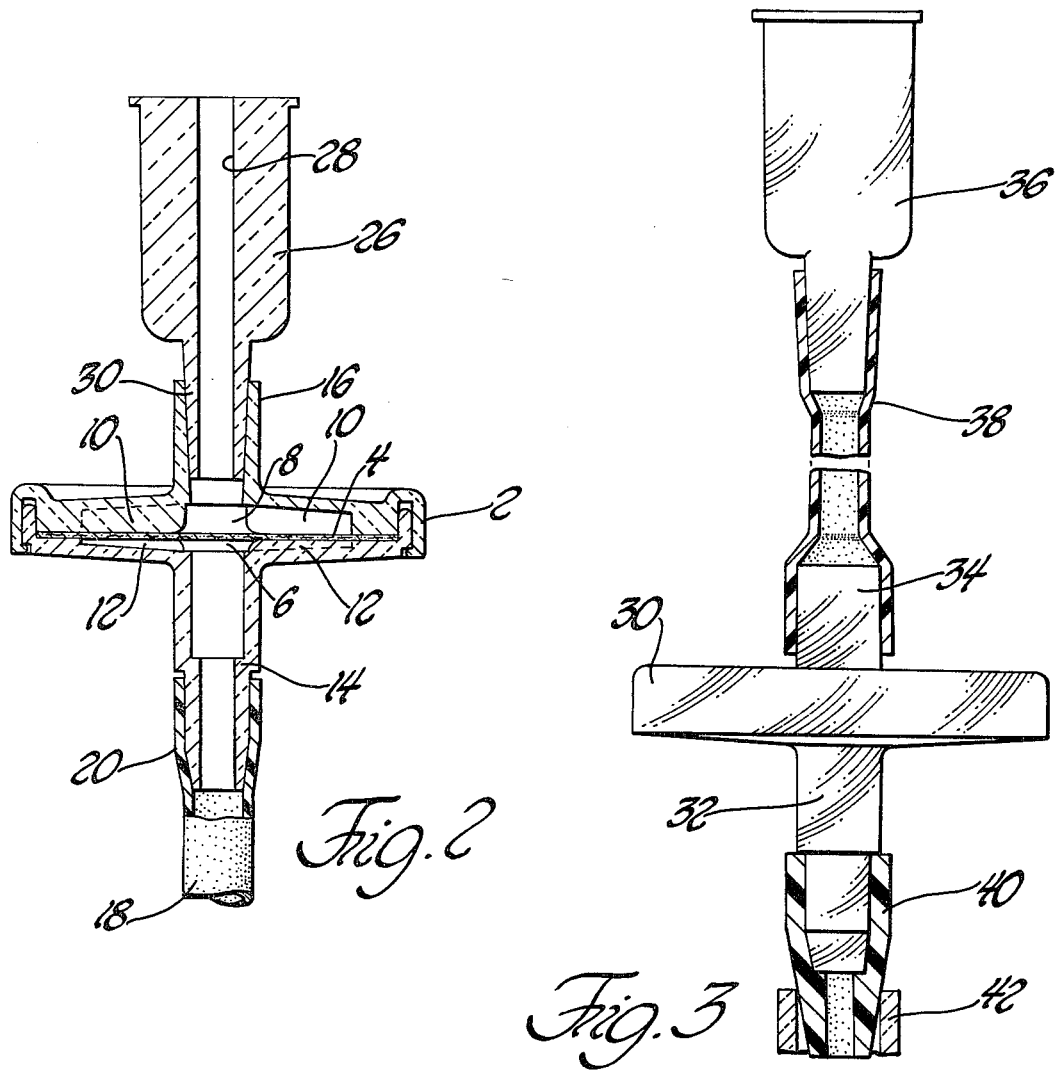
Fig. 2
Fig. 3

MOUTH FILTER FOR USE WITH PIPETTES

This patent application is a continuation-in-part of patent application Ser. No. 768,450 filed Feb. 14, 1977, now abandoned.

The subject matter of the present invention is a mouth filter device for use with pipettes which in use require mouth-applied suction to draw a liquid into the pipette.

Chemists, biologists, and others skilled in the art readily appreciate the hazard involved in the careless use of a pipette. That is, if while using a pipette the technician's attention is distracted from the task at hand—that of drawing liquid into the pipette by the application of mouth-applied suction—it is easily possible for the technician to end up with a mouthful of the liquid being drawn. Many have been the chemistry students and chemists who have had to spit out some acid or other harmful chemical as the result of the use of a pipette without close attention. In the areas of biology, microbiology, and the medical profession, there is the still further hazard, in the use of a pipette, of the ingestion of harmful bacteria present in the liquid being drawn into the pipette. Protection for the technician is here required, not just against the careless use of the pipette but even when the technician uses the pipette with utmost care. That is, the biologist or medical technician might, on occasion, be sucking into the pipette a liquid pregnant with harmful bacteria which, absent protection, could reach the mouth, by way of the vapor above the liquid, albeit the pipette would be carefully used such that the liquid itself did not reach the mouth.

The present invention provides a practical, low-cost device for protecting the chemist, biologist, medical technician or other person using a pipette or the like from the aforesaid hazards.

The invention will now be described in detail, in part by reference to the accompanying drawings in which:

FIG. 1 is a perspective view of a mouth filter device made in accordance with the invention;

FIG. 2 is a side view in cross-section, and in somewhat enlarged scale, of a portion of the device shown in FIG. 1; and FIG. 3 is a perspective view of another embodiment of the invention.

Referring now to FIGS. 1 and 2, the mouth filter device of the present invention comprises a flat, cylindrical, rigid, transparent organic resin housing 2, there being a round filter membrane 4 extending transverse to the axis of the housing and in sealed relationship with the cylindrical side wall of the housing. Hence, the filter membrane divides the housing into an inlet chamber 6 on one side of the filter membrane and an exit chamber 8 on the other side of the filter membrane. For ample support of the filter membrane, which may be of relatively delicate construction, the housing can be provided with circumferentially spaced, radially extending upper and lower ribs, 10 and 12 respectively, which contact the membrane and provide the desired physical support. The housing can be constructed of upper and lower transparent organic resin moldings which are snapped together with the membrane therebetween, as shown, after which the molding can be heat sealed together around the circumference thereof so as to provide a hermetic seal.

The filter membrane 4 must be hydrophobic, i.e. it must be such that it enables the passage therethrough of gas but prevents the passage therethrough of liquid. Still further, the filter membrane must constitute a bacteria barrier, which means that the filter membrane must have a submicron pore size sufficiently small to block the migration of bacteria from one side to the other thereof. Such hydrophobic bacteria-barrier membranes are already known in the art and are commercially available, as exemplified by the filter membrane marketed by the assignee of the present invention under the trademark "Acropor", such membrane having a pore size of from about 0.2 to 0.5 microns. Such a filter membrane consists of a unitary organic resin film, typically 0.005 inches in thickness, having random and irregular passages therethrough of sufficiently small dimensions to block the passage of anything, including bacteria, having a size greater than the aforesaid 0.5 microns.

Extending axially from and integral with one axial end of the housing and communicating with the inlet chamber 6 is a tubular extension 14. Extending axially from and integral with the opposite axial end wall of the housing is a tubular extension 16 which communicates with the exit chamber 8.

Connected to and communicating with the tubular extension 14 is a flexible elastomeric tube 18. The end 20 of the elastomeric tube 18 is, in its unstretched condition, of somewhat lesser internal diameter than the external diameter of the lower end of the housing extension 14 and is sealingly secured thereto simply by way of its inherent resiliency which provides an excellent mechanical and leak-free connection. The opposite end 22 of the flexible tube is adapted to be fitted in sealed relationship to the upper end 24 of a pipette into which it is desired to draw the liquid. The connection between the end 22 of the flexible tube and the upper end 24 of the pipette is similar to the connection between the end 20 of the flexible tube and the tubular projection 14 of the filter membrane housing. That is, the normal unstretched internal diameter of the flexible tube is somewhat less than the external diameter of the upper end of the pipette, and the attachment of the end of the flexible tube to the pipette is accomplished by a stretching of the end of the elastomeric tube thereby providing a good mechanical and leak-proof, though rapidly detachable, connection.

Connected to the tubular extension 16 is a molded organic resin mouthpiece 26. The mouthpiece has an opening 28 therethrough which communicates with the passage through the extension 16 and hence communicates with the exit chamber of the filter membrane housing. In the embodiment shown in FIGS. 1 and 2, there is a friction fit between the tapered outer surface of the lower end 30 of the mouthpiece and the tapered interior surface of the extension 16, the friction fit being ample to maintain the mouthpiece secured to the extension in sealed relationship therewith.

It is preferred that the flexible tube be at least about 12 inches long so that when the flexible tube is connected to the pipette, the technician who, with his mouth draws the vacuum through the mouthpiece, can be this distance away, laterally, from the pipette so as to be able to clearly view the liquid level attained in the pipette as the mouth suction is applied. On the other hand, a tube length of greater than 24 inches is cumbersome and serves no useful purpose.

In operation, the chemist, biologist, or other technician connects the end of the flexible tube to the pipette and then, with the pipette inserted into the liquid desired to be drawn, applies mouth suction to the mouthpiece 26 until the desired level of the liquid in the pipette is attained. But in the event the technician's attention should be distracted, the filter membrane 4 absolutely insures against the liquid being drawn into the technician's mouth since the filter membrane 4 is hydrophobic and hence blocks the pasage of any liquid—though allowing the passage of gas therethrough. As regards use by biologists where the liquid being drawn into the pipette might contain virulent bacteria, the filter membrane of the device, being a bacteria barrier, fully protects the technician against the ingestion of the bacteria even though such bacteria might be present in the vapor phase above the liquid. Hence, the device of the present invention provides a low-cost, convenient way to protect technical personnel who are required, by mouth-applied suction, to withdraw liquid chemical or biological samples into pipettes.

The FIG. 3 embodiment differs from that of FIGS. 1 and 2 chiefly in that when in use, the filter membrane is located more closely adjacent the pipette. Referring to FIG. 3, the filter housing 30, the filter membrane (not shown) therein and the inlet and outlet tubular extensions, 32 and 34 respectively, of the housing are all identical in structure to the like components shown in the FIGS. 1-2 embodiment; however, in the FIG. 3 embodiment the mouthpiece 36 is connected to the outlet tubular extension 34 of the filter housing by a flexible elastomeric tube 38 which can be the same as, but preferably shorter than, the flexible elastomeric tube 18 of the FIGS. 1-2 embodiment. Connected to the inlet tubular extension 32 of the filter housing is an elastomeric tube 40 which is of generally conical external shape. The tube can be relatively short—about ¾ inch to 1 inch, for example. When the FIG. 3 embodiment is used, the conical elastomeric tube 40 is inserted into the upper end of the pipette until a good seal is accomplished between the pipette and the elastomeric tube 35 which is relatively soft and hence enables a good seal. Because of the conical shape of the elastomeric tube 40, the filter can be used with any of a variety of different sized pipettes having different diameters, the elastomeric tube extending only a short distance into a pipette of small diameter and extending further into a pipette of larger diameter. In FIG. 3, 42 is the upper end of the pipette into which the conical tube 40 has been inserted.

It will be understood that whereas the invention has been described in its particulars with reference to preferred embodiments thereof, various changes and modifications may be made all within the full and intended scope of the claims which follow.

The embodiments of the present invention in which an exclusive property or privilege is claimed are defined as follows:

1. A mouth filter device for use with pipettes where suction is applied by the mouth to draw liquid into the pipette, said device comprising a flat, cylindrical, organic resin housing, a round filter membrane in and extending transverse to the axis of said housing and in sealed relationship with said housing so as to divide said housing into an inlet chamber on one side of said filter membrane and an exit chamber on the other side of said filter membrane, said filter membrane being hydrophobic thereby to allow the passage of gas therethrough while preventing the passage of liquid therethrough and said filter membrane having a submicron pore size sufficiently small to prevent the passage of bacteria therethrough, a tubular extension on and integral with one axial end of said housing extending axially from and communicating with said inlet chamber, a tubular extension on and integral with the other axial end of said housing extending axially from and communicating with said exit chamber, an elastomeric tube having one end thereof connected and communicating with said first mentioned extension, the other end of said tube being adapted to be fitted in sealed relationship to the pipette, and an organic resin mouthpiece connected to said second mentioned tubular extension and having an opening therethrough communicating with said exit chamber whereby mouth-applied suction to said mouthpiece creates suction through the filter membrane and said tube to draw liquid into the pipette to which the tube is fitted thereby to draw liquid thereinto, said filter membrane assuring against any of the liquid or any bacteria therein reaching the mouth.

2. A device as set forth in claim 1 wherein said mouthpiece is connected directly to said first mentioned extension.

3. A device as set forth in claim 1 wherein said elastomeric tube has a conical shaped outer surface for insertion into a pipette in sealed relationship therewith and wherein said mouthpiece is connected to said first mentioned extension by a flexible tube.

* * * * *